United States Patent [19]

Glaze

[11] Patent Number: 5,118,630
[45] Date of Patent: Jun. 2, 1992

[54] METHOD FOR DETERMINING PERIODIC INFERTILITY IN FEMALES

[75] Inventor: Thomas A. Glaze, Palo Alto, Calif.

[73] Assignee: Quidel Corporation, San Diego, Calif.

[21] Appl. No.: 267,148

[22] Filed: Nov. 4, 1988

[51] Int. Cl.⁵ .............................................. G01N 33/48
[52] U.S. Cl. ..................... 436/65; 436/510; 436/518; 436/817; 436/906; 435/7.1
[58] Field of Search ............ 435/7; 436/518, 528, 436/547, 65, 164, 169, 807, 808, 817, 906; 422/55, 56, 58, 61

[56] References Cited

U.S. PATENT DOCUMENTS

Re. 32,557  12/1987  Chatterton ............................. 435/28
4,508,830   4/1985   Baker et al. ............................ 435/7

FOREIGN PATENT DOCUMENTS 75193    3/1983  European Pat. Off.
1228442  4/1969  Fed. Rep. of Germany.
8802505  7/1988  Sweden.
1604863  12/1981 United Kingdom.

OTHER PUBLICATIONS

Barnard et al., *Chemical Abstracts*, vol. 95:111238q (1981).
Eshhar et al., *Steroids*, vol. 38(1), pp. 89–109 (1981).
Hoffmann et al., *Fertility and Sterility*, vol. 40(3), pp. 417–418 (1983).
Shah et al., *Clinical Chemistry*, vol. 30(2), pp. 185–187 (1984).
Hiroi et al., *Gynecol. Obstet. Invest.*, vol. 22, pp. 186–193 (1986).
Anthony et al., *Human Reproduction*, vol. 3(7), pp. 870–872 (1988).
Brown et al., *Chemical Abstracts*, vol. 110:18596y (1989).
Brown et al. (1987) Am. J. Obstet. Gynecol. 157:1082–1098.
Collins et al. (1981) Proc. Xth Int'l Cong . . . . . pp. 19–33.
Samarajeewa et al. (1983) The Urinary Assay . . . pp. 414–421.
ProgestURINE PDG Assay, Monoclonal Antibodies, insert.
Denari et al. (1981) Obstet. Gynecol. 58:5–9.

*Primary Examiner*—Sam Rosen
*Attorney, Agent, or Firm*—Townsend and Townsend

[57] ABSTRACT

A natural birth control method comprises observance of the first day of menses followed by measurement of urinary progesterone metabolite levels beginning a predetermined number of days after the first day of menses. Urinary progesterone metabolite measurement is performed on days of planned sexual activity until the concentration level exceeds a threshold value indicative of ovulation occurring more than 24 hours previously. Once such a threshold value is observed, the woman may discontinue testing and can consider herself unable to conceive until after the beginning of the subsequent menstrual cycle.

4 Claims, 1 Drawing Sheet

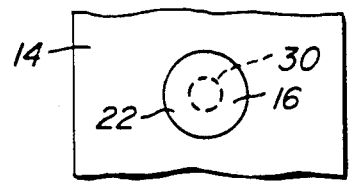
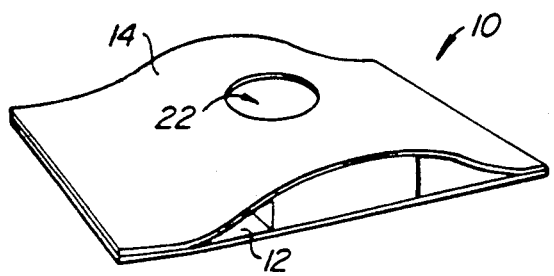
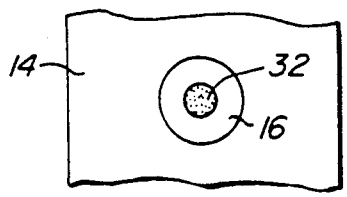
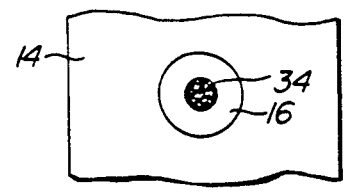
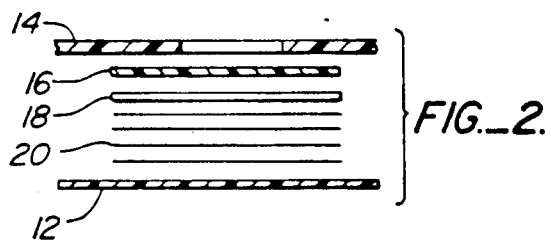
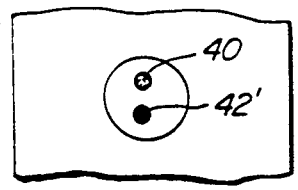
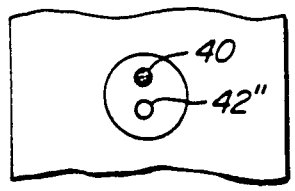

METHOD FOR DETERMINING PERIODIC INFERTILITY IN FEMALES

BACKGROUND OF THE INVENTION

1. Field of the Invention

The present invention relates generally to methods and kits for determining the occurrence of periodic infertility in women. More particularly, the present invention relates to the detection of a threshold level of pregnanediol glucuronide in urine which indicates that the woman will be unable to conceive until after the occurrence of menses.

For religious, ethical, and medical reasons, a significant number of women have elected against employing contraceptive drugs and devices and instead rely on natural family planning methods for birth control. Additionally, other women and couples who utilize barrier methods of contraception often wish to determine those times, when such protection is not needed. In general, natural family planning methods rely on the woman observing certain physiological indicators, such as basal body temperature and cervical mucous consistency, to determine the time of ovulation. By refraining from intercourse for an appropriate period before and after ovulation, conception can usually be avoided. Because of variations in the woman's cycle, however, reliance on basal body temperature and the appearance of the cervical mucous is not always effective, and it would therefore be desirable to have more reliable physiological indicators.

Alternative indicators have been suggested. For example, it is known that a surge in the woman's level of luteinizing hormone (LH) is predictive of ovulation. Further, it is known that the woman's levels of progesterone are elevated a short time after ovulation. Thus, it has been suggested that by first determining the occurrence of the LH surge, and subsequently determining the presence of elevated levels of pregnanediol glucuronide (PDG, a progesterone metabolite) in urine, the time during which a woman is fertile, or conversely is infertile, may be determined.

Such two-step determinations, however, suffer from certain deficiencies. For example, the LH surge does not always occur, rendering the determination of fertile and infertile periods problematic. Second, the need to perform two distinct types of measurements complicates the determination of fertility, rendering it less useful.

For these reasons, it would be desirable to provide infertility assays which are simple to perform, preferably relying on a single type of measurement. Such assays should be a highly reliable indicator of infertility, and will preferably be combined with the observation of other physiological indicators, such as menses, in order to determine the entire period of infertility.

2. Description of the Background Art

Brown et al. (1987) Am. J. Obstet. Gynecol. 157:1082–1089 describe how a woman's period of fertility may be determined based on measurements of estrogen and pregnanediol glucuronides in urine. Enzyme assays for estrogen are used to detect the beginning of the fertile period while enzyme assays for pregnanediol glucuronides are used to detect the end. The pregnanediol glucuronide assay was positive for concentrations above 5.2 $\mu$mol/24 hr. (equivalent to about 1.7 $\mu$g/ml based on 1500 ml of urine). Collins et al. (1981) Proc. Xth Int'l Congress on Fertility and Sterility, MTP Ltd., pp 19–33, suggests that a woman's period of fertility may be determined by first measuring luteinizing hormone or estradiol peak followed by measurement of steroid glucuronides, such as pregnanediol-3$\alpha$-glucuronide. Methods for the detection of steroid glucuronides in urine are described in Samarajeewa et al. (1983) *The Urinary Assay of Steroid Glucuronides: Their Value and Methodology for Clinical Chemistry*, 2nd Ed., Churchill Livingston, Edinburgh pp. 414–421. A solid phase competitive colorimetric immunoassay for 5b-pregnane-3$\alpha$-20$\alpha$-diol glucuronide is commercially available from Monoclonal Antibodies, Inc., Mountain View, Calif., under the tradename ProgestURINE PDG Assay. The assay is described in an accompanying package insert. A radioimmunoassay for measuring pregnanediol-3-glucuronide in urine is described in Denari et al. (1981) Obstet. Gynecol. 58:5–9, where it is further described that metabolite levels in early morning urine samples have the highest correlation with serum levels of the corresponding hormone.

SUMMARY OF THE INVENTION

According to the present invention, a method for determining periodic infertility in human females begins by observing the first day of menses in the menstrual cycle. A predetermined time following the first day of menses, the level of a progesterone metabolite, usually pregnanediol glucuronide (PDG) in urine can be measured as an indicator of fertility. If the PDG level is found to have exceeded a predetermined threshold value, usually about 3.5 $\mu$g/ml, the woman is considered to be unable to conceive from intercourse occurring on that day until at least the first day of menses in the following menstrual cycle. Testing need only be performed on days prior to planned sexual activity, and by testing only within the prescribed period, maximum economy is achieved.

The present invention also comprises a kit for performing the above-described method. The kit will include components and reagents necessary to perform a plurality of PDG assays as well as instructions on when and how to perform the assays and how to interpret the results to detect the infertile portion of the woman's menstrual cycle.

BRIEF DESCRIPTION OF THE DRAWINGS

FIG. 1 is a perspective view of a reaction cell useful for performing a PDG assay according to the method of the present invention.

FIG. 2 is an exploded cross-sectional view of the reaction cell of FIG. 1.

FIGS. 3A–3C illustrate the results obtained using a first colorimetric assay protocol to measure PDG.

FIGS. 4A and 4B illustrate the results obtained using a second colorimetric assay protocol to measure PDG.

DESCRIPTION OF THE SPECIFIC EMBODIMENTS

The present invention is a natural birth control method which relies on combining the observance of the woman's physiological condition, i.e., the onset of menses, with quantitative measurement of a single hormonal level, i.e., the level of a urinary progesterone metabolite. The first day of menses serves as a marker or base day, and measurement of the urinary progesterone metabolite should commence no sooner than a predetermined number of days following the base day. The length of separation between the first day of menses and the measurement of the urinary progesterone metabolite is based on the average length of the woman's menstrual period (cycle). The length may be determined based on the following relationship which has been established to provide a high degree of certainty that the initial progesterone metabolite elevation will not be missed, while minimizing premature testing for the metabolite.

| Cycle Length | Start Testing | Cycle Length | Start Testing |
|---|---|---|---|
| 21-22 | 11 | 32 | 20 |
| 23-24 | 12 | 33 | 21 |
| 25 | 13 | 34 | 22 |
| 26 | 14 | 35 | 23 |
| 27 | 15 | 36 | 24 |
| 28 | 16 | 37 | 25 |
| 29 | 17 | 38 | 26 |
| 30 | 18 | 39 | 27 |
| 31 | 19 | 40 | 28 |

Once begun, the progesterone metabolite measurements are continued on a daily basis until the measured level is found to exceed a predetermined threshold value which indicates that ovulation occurred at least 24 hours previously, preferably at least 36 hours previously, and more preferably at least 48 hours previously. As the ovum is viable for a maximum of 24 hours after ovulation, intercourse more than 24 hours after ovulation will not likely result in conception.

Suitable urinary progesterone metabolites include both pregnanediol-3α-glucuronide (PDG) and pregnanetriol-3α-glucuronide (PDT), with measurement of PDG being preferred as it is present in higher concentrations. It will be appreciated, however, that the measurement of PDT is also suitable with appropriate modification of the threshold level, as discussed hereinbelow.

The threshold level of PDG is selected to be sufficiently high to assure that ovulation has occurred at least 24 hours previously, while being sufficiently low so that it is able to detect elevated PDG levels even in women where the levels are not particularly high. It has been found that a PDG measurement in the range from about 2 to 5 μg/ml is suitable, with a 3.5 μg/ml threshold level being preferred. The PDG measurement should be made at the same time each day, preferably from a specimen of the first urine in the morning.

A variety of conventional systems are available for effecting PDG measurement, including radioimmunoassay, enzyme immunoassay, and the like. As the tests will normally be performed in the home by untrained individuals, however, it is preferred that the tests be rapid and require no instrumentation. Particularly suitable are solid phase immunoassays having an enzyme-catalyzed color end point which can be visually observed and interpreted by the user. Such tests should be sufficiently sensitive and calibrated so that the threshold level of the progesterone metabolite can be observed. Usually, the test will provide for a positive/negative interpretation, correlated with the fertile or infertile portions of the woman's menstrual cycle.

Particularly preferred are solid phase membrane assays of the type described in U.S. patent application Ser. No. 128,257, filed Dec. 3, 1987, and Ser. No. 128,260, filed Dec. 3, 1982, assigned to the assignee of the present invention, the disclosures of which are incorporated herein by reference. Such assay systems can be adapted to run competitive immunoassays for PDG as follows.

Referring to FIGS. 1 and 2, a reaction cell 10 includes a base panel 12 and an upper panel 14. Interposed between the panels 12 and 14 are a microporous membrane 16, a spacer layer 18, and an adsorbent 20 comprising a plurality of layers of non-woven cellulose. Conveniently, the base and upper panels 12 and 14 are formed from a thermoplastic, such as polystyrene, and may be heat sealed along their edges to form the reaction cell 10. Upper panel 14 includes an aperture 22 which exposes the upper surface of membrane 16 to the exterior of the reaction cell 10. The urine sample and necessary reagents, as described in more detail hereinbelow, may be added to the solid phase membrane 16 through aperture 22, with the adsorbent 20 acting as a wick and drawing the solutions through the membrane 16.

Membrane 16 acts as a solid phase in supporting immobilized anti-PDG antibodies thereon. Suitable antibodies may be monoclonal or polyclonal, and may be prepared by conventional techniques relying on the hyperimmunization of an invertebrate host with PDG immunogens. Particular methods for preparing antibodies against PDG are taught in Samarajeewa et al. (1981) Steroids 38:667-678. A particularly suitable membrane is a nylon membrane having an aperture pore diameter of 3 μm.

Once prepared, isolated, and purified, the anti-PDG antibodies may be immobilized on a membrane by suitable techniques, including adsorption and covalent binding. In either case, the antibodies should be immobilized at a concentration sufficient to allow differentiation between urine sample having PDG levels below and above the concentration range from 2 to 5 μg/ml.

A suitable immobilization protocol is as follows.

Anti-PDG antibodies are prepared in a suitable buffer at a concentration in the range from about 2 to 6 mg/ml and immobilized by depositing 1 to 3 μl of the antibody solution onto membrane 16. A reactive spot is formed on membrane 16 having a typical diameter of 2 to 5 mm. Unoccupied binding sites on the surrounding portion of membrane 16 are then blocked by the addition of 200 to 400 μl of a non-specific protein solution, usually not-fat dry milk, at a concentration of between 10 and 50 mg/ml. Reaction cells 10 with immobilized anti-PDG antibodies are dried and packaged in a moisture-free condition.

The reaction cell 10 just described is suitable for performing competitive binding assays where the urine sample is first applied to the membrane followed by application of a suitable enzyme-PDG conjugate. The free PDG in the urine sample and the enzyme-PDG conjugate compete for limited anti-PDG binding sites on the membrane so that the amount of enzyme bound to the membrane is determined by the relative amount of free PDG present in the urine sample. After sufficient time for binding equilibrium to be reached, excess free PDG and enzyme-PDG conjugate are removed by washing, and enzyme substrate is then applied to the membrane. The enzyme and substrate system are chosen to result in the production of a colored product which is deposited on the membrane. As the amount of enzyme bound is inversely proportional to the amount of free PDG in the urine sample, the color intensity on the membrane 16 will be inversely proportional to the PDG concentration in the urine. That is, an intense color is indicative of low or no PDG in the urine sample, while no or low color is indicative of high PDG in the urine sample.

Numerous suitable signal producing systems are described in U.S. Pat. No. 4,366,241 at column 27, line 35 through column 36, line 63, the disclosure of which is incorporated herein by reference. Preferred are the use of color-producing systems which result in the deposition of a dye on the membrane, such as PDG-alkaline phosphatase conjugate with indoxyl phosphate substrate which results in deposition of a dark blue dye on the membrane surface.

Referring now to FIGS. 3A-3C, antibody will typically be applied to only a limited portion of the exposed membrane area on the reaction cell, such as within a circular region bounded by broken line 30 as shown in FIG. 3A. When performing the assay as described above, high PDG levels, typically above 4 µg/ml will result in little or no color on membrane 16, as shown in FIG. 3A. Such a result will indicate that ovulation occurred more than 24 hours previously and that the user will be unable to conceive until after the beginning of the next menstrual cycle.

A urinary concentration of PDG at about 2 µg/ml will result in a spot 32 having moderate intensity, as illustrated in FIG. 3B, while PDG levels significantly below 2 µg/ml will result in an intensely colored spot 34, as illustrated in FIG. 3C. Generally, the user would expect to progress from the dark spot 34 through the moderate spot 32 until only a faint spot or no spot at all appears on the membrane 16. A calibration chart, provided with the assay kit of the present invention, will help the user to determine which portion of her cycle she is in at the time of the test. Generally, the woman will be unable to conceive from the time the moderately colored spot 32 first appears until after the beginning of her next menstrual cycle, usually for a period of from 3 to 4 days following the first day of menses.

As an alternative to the system of FIGS. 3A-3C, the reaction cell 10 of the present invention may be provided with a control spot on the membrane 16. As illustrated in FIGS. 4A and 4B, control spot 40 is produced by immobilizing a concentration of the enzyme which corresponds to a urinary PDG level at the threshold value, typically 3 µg/ml (which is just below the desired positive threshold value for the test spot). Thus, as the assay protocol is carried out, color is produced within the control spot which corresponds to the precise intensity associated with the threshold of PDG value. Prior to ovulation and for the first approximately 24 hours following ovulation, the test spot 42' (FIG. 4A) which results from the application of the urine sample will be more intense than the control spot 40, indicating that the woman has not entered into her infertile period. More than 24 hours after ovulation, however, the test spot 42" will appear as in FIG. 4B, and the reduced intensity relative to the control spot 40 will indicate that the woman has entered into her infertile period. The use of control spots is generally preferred as it eliminates any variation in color intensity which might result from differences in the activity of the reagents and in the manner in which the test is performed by the user.

In a third alternative format, a reference spot comprising anti-enzyme antibodies can be provided on the reaction cell membrane. Such a reference spot does not provide a concentration control, as described above. Instead, a positive reading within the reference spot indicates that the steps of the assay have been correctly performed. The anti-enzyme antibodies bind the enzyme-PDG conjugate and provide for color deposition so long as the assay steps have been correctly performed.

Although the foregoing invention has been described in some detail by way of illustration and example for purposes of clarity of understanding, it will be obvious that certain changes and modifications may be practiced within the scope of the appended claims.

What is claimed is:

1. A method for determining periodic infertility in human females, said method comprising:
   observing the first day of menses in the female;
   determining the concentration of pregnanediol-3α-glucuronide (PDG) or pregnoatriol-3α-glucuronide (PTG) in urine of the female using an immunoassay, said determinations being made commencing a predetermined time after the first of day menses, wherein the days between the first day of menses and the first day of metabolite determination are calculated according to the following relationship:

| Cycle Length | Start Testing | Cycle length | Start Testing |
|---|---|---|---|
| 21-22 | 11 | 32 | 20 |
| 23-24 | 12 | 33 | 21 |
| 25 | 13 | 34 | 22 |
| 26 | 14 | 35 | 23 |
| 27 | 15 | 36 | 24 |
| 28 | 16 | 37 | 25 |
| 29 | 17 | 38 | 26 |
| 30 | 18 | 39 | 27 |
| 31 | 19 | 40 | 28 | observing if the concentration of the metabolite exceeds a threshold level indicative of ovulation; and
   observing the occurrence of the subsequent menses in the female;
   whereby the female is considered incapable of conception from sexual activity which occurs from the time the threshold concentration is exceeded until at least the subsequent occurrence of menses.

2. A method as in claim 1, wherein the threshold level of PDG is at least about 3.5 µg/ml.

3. A method as in claim 1, wherein the threshold level is in the range from about 2 µg/ml to 5 µg/ml.

4. A method as in claim 1, wherein the level of PDG is determined by a solid phase immunoassay having a colorimetric end point.

* * * * *